Figure 1:
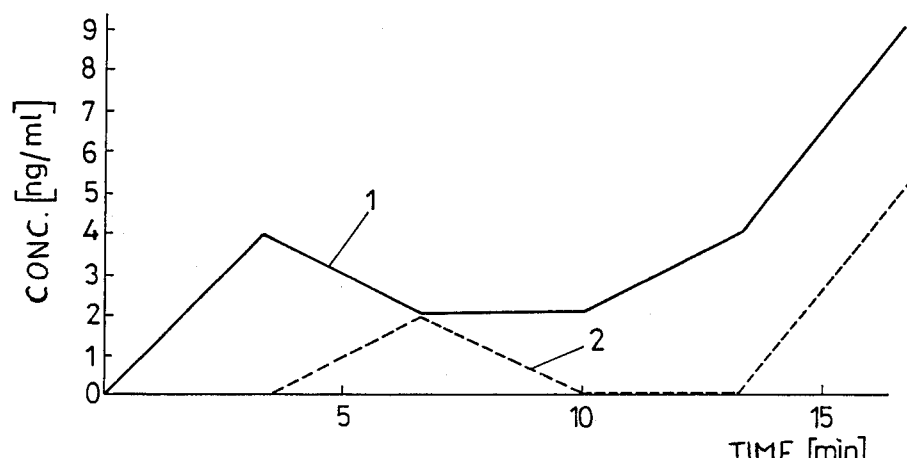
Figure 2:
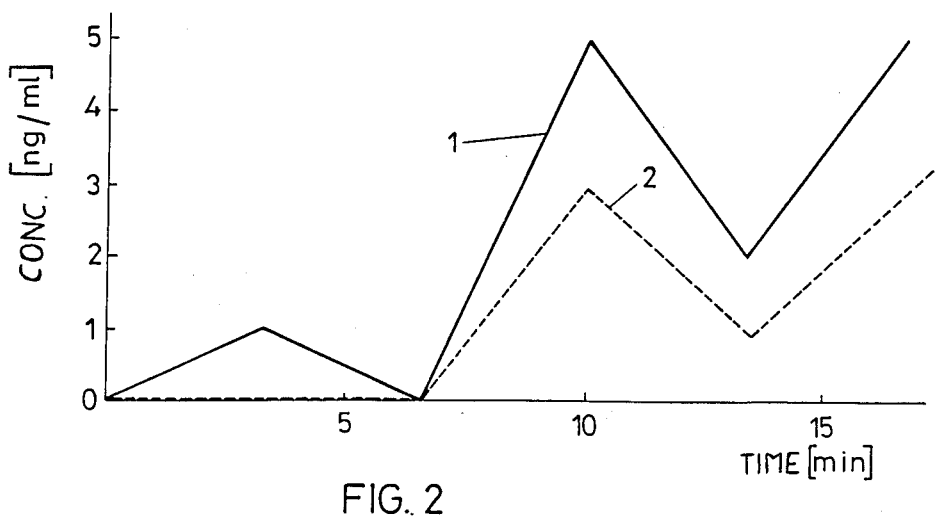
Figure 3:
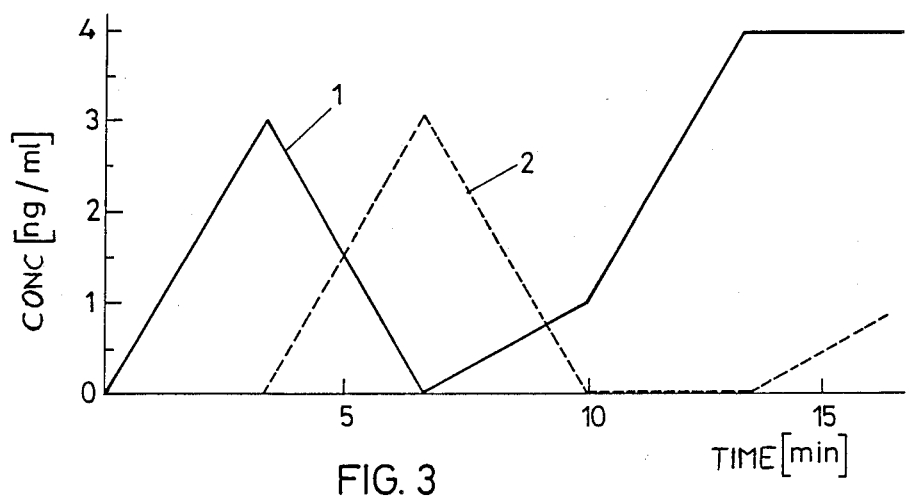
Figure 4:
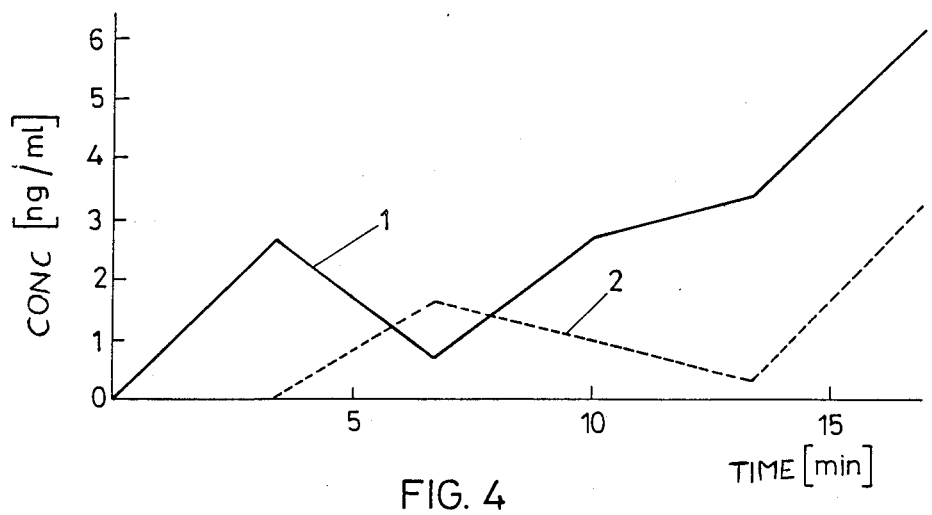
Figure 5:
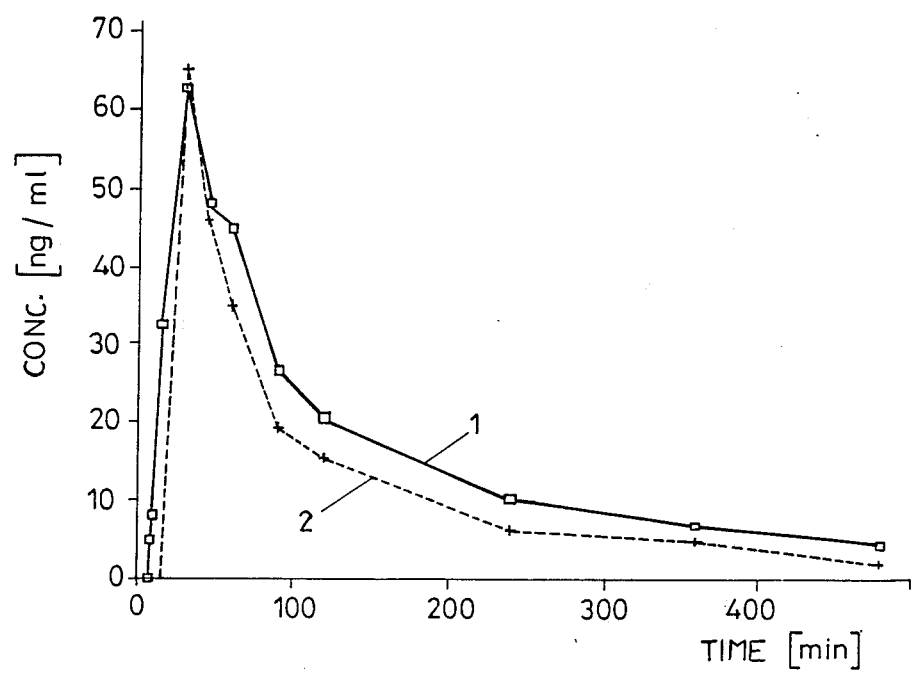
Figure 6:
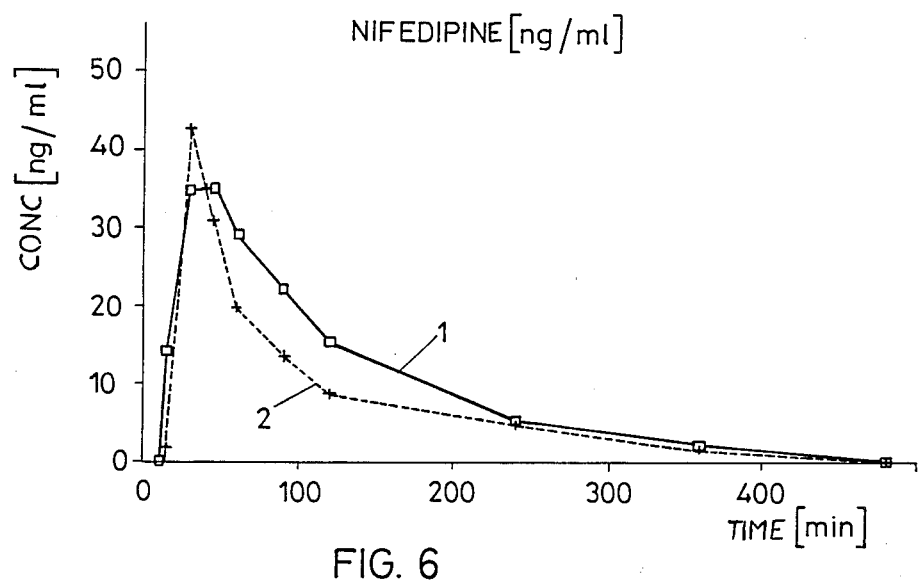
Figure 7:
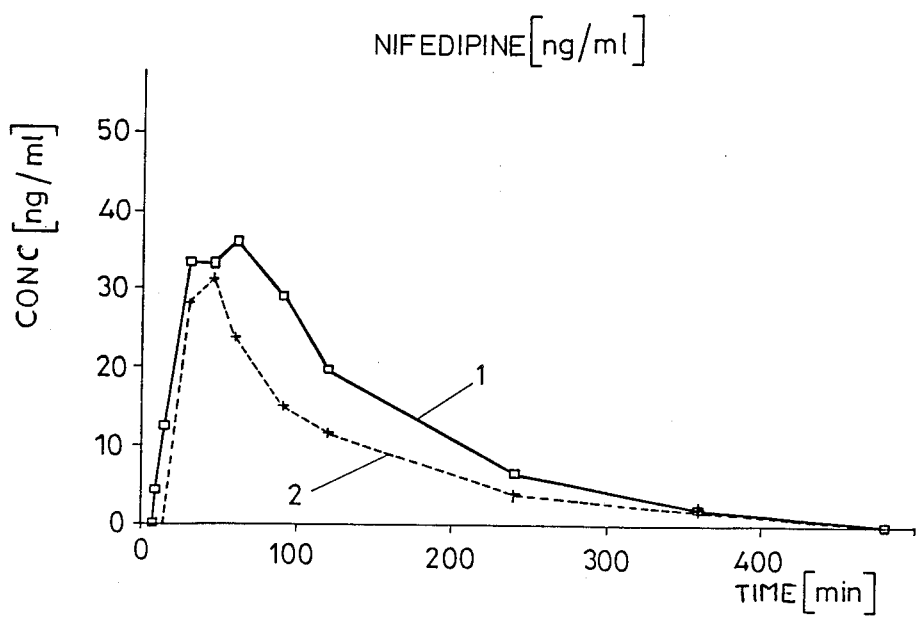
Figure 8:
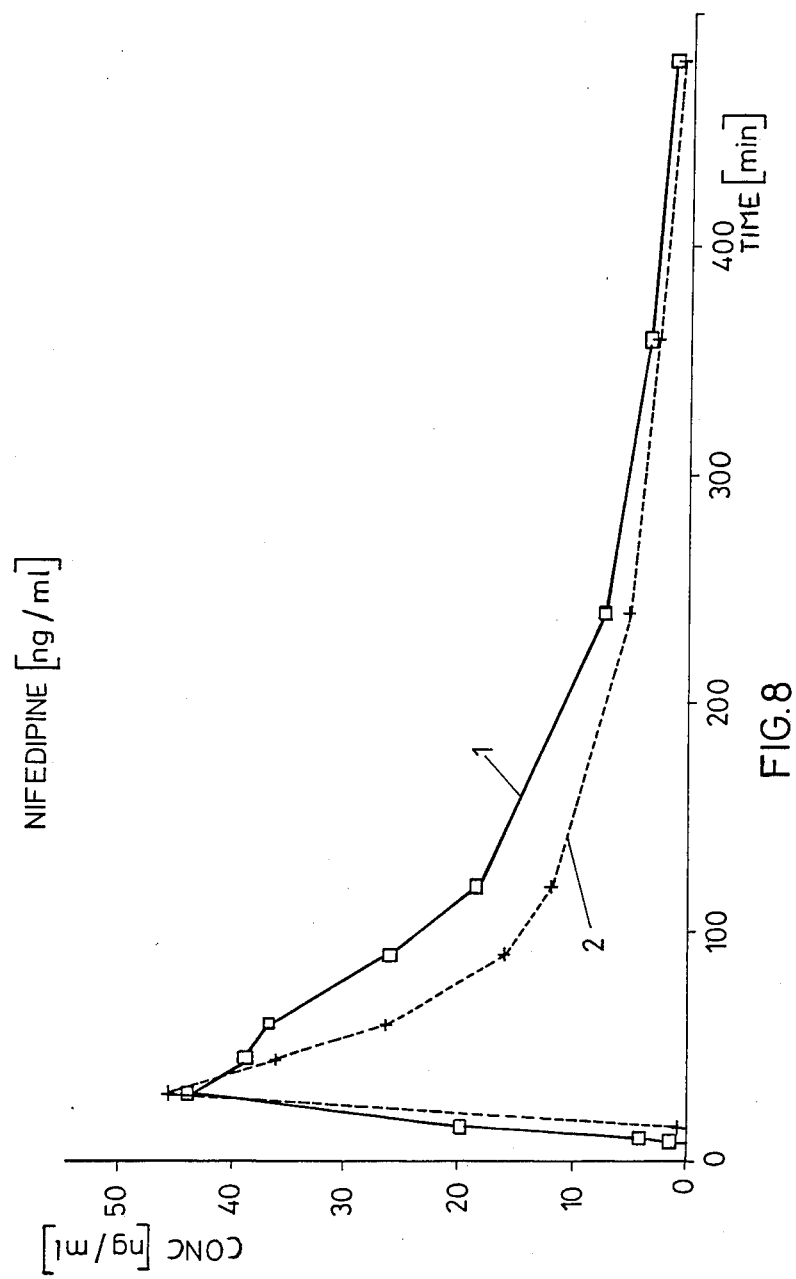

United States Patent [19]

Burghart et al.

[11] Patent Number: 4,869,899
[45] Date of Patent: Sep. 26, 1989

[54] PHARMACEUTICAL PREPARATION AND PROCESS FOR PRODUCING THE SAME

[76] Inventors: Walter Burghart, Salmgasse 4, A-1030 Vienna; Kurt Burghart, Saegeberg 8, D-2217 Rosdorf, both of Austria

[21] Appl. No.: 131,138
[22] PCT Filed: Mar. 10, 1987
[86] PCT No.: PCT/AT87/00016
§ 371 Date: Nov. 10, 1987
§ 102(e) Date: Nov. 10, 1987
[87] PCT Pub. No.: WO87/05211
PCT Pub. Date: Sep. 11, 1987

[30] Foreign Application Priority Data

Mar. 10, 1986 [AT] Austria .................................. 620/86
Nov. 19, 1986 [AT] Austria ................................. 3092/86

[51] Int. Cl.$^4$ ............................................. A61K 31/74
[52] U.S. Cl. ........................................ 424/78; 424/80
[58] Field of Search ................................... 424/78, 80

[56] References Cited

U.S. PATENT DOCUMENTS 4,442,112 4/1984 Muller-Schweinitzer .......... 514/338

FOREIGN PATENT DOCUMENTS 0117888 9/1984 European Pat. Off. .
0175671 3/1986 European Pat. Off. .
2822882A1 6/1978 Fed. Rep. of Germany .
3307422A1 5/1984 Fed. Rep. of Germany .
2162745 2/1986 United Kingdom .

OTHER PUBLICATIONS

Wu Bai Ming, et al, "Rapid Antihypertension Effects of Nifedipine Spray", Chinese Journal of Cardiovascular Diseases, 1980, vol. 8, No. 3, pp. 1–9.
G. R. Brown et al, "Nifedipine Serum Concentrations Following Sublingual and Oral Doses", Int'l Journal of Clinical Pharmacology, Therapy and Toxicology, vol. 24, No. 6–1986 (pp. 283–286).

Primary Examiner—Joseph L. Schofer
Assistant Examiner—Carmen Pili-Curtis
Attorney, Agent, or Firm—Nixon & Vanderhye

[57] ABSTRACT

A pharmaceutical preparation contains an active ingredient added to polyalcohols, such as polyethylene and/or polyalkylene glycols and/or oxystearates of glycerine-polyethyleneglycol and/or partial fatty acid esters of sorbitan or polyhydroxyethylenesorbitan and/or polyvinylpyrrolidone and/or polyvinylalcohols and/or fatty alcohol ethers of polyhydroxyethylene or fatty acid ester of polyhydroxyethylene and/or condensates of polyhydroxyethylene-polyhydroxypropylene, and especially dissolved in nifedipine in a weight ratio between 1:2 and 1:25. The composition contains ethanol as well, in an amount ratio between 1:25 and 1:4 of nifedipine:ethanol and can be sprayed with a propeller gas.

17 Claims, 10 Drawing Sheets

PHARMACEUTICAL PREPARATION AND PROCESS FOR PRODUCING THE SAME

The present invention relates to a pharmaceutical composition containing nifedipine as the active constituent and to a process for the preparation of a sublingual dosable adminstrable pharmaceutical composition with nifedipine as the active constituent.

Nifedipine is an established therapeutical agent for coronary heart disease and solid formulations containing nifedipine together with processes for their manufacture have become common knowledge, for example through DE-OS 28 22 882. Nifedipine: 4-(2-nitrophenyl)-2,6-dimethyl-3,5-dicarboxymethoxy-1,4-dihydropyridine is known to be extremely light-sensitive and there have been a number of suggestions for administering this compound so as to prevent photo-decomposition and the associated reduction in efficacy. DE-OS 28 22 882 discloses a formulation in which solid nifedipine is mixed with polyvinylpyrrolidine, methyl cellulose, hydroxypropyl cellulose and hydroxypropylmethyl cellulose, accompanied by additional surfactants, in particular oils. This method of application was chosen in the first instance in order to improve the bioavailability of the drug following administration but is nevertheless associated with considerable disadvantages in terms of stability and photosensitivity. For oral administration, capsules have been suggested as an alternative to tablets/pills, with incorporation of dyes into the capsule shells in order to overcome photo-degradation. Such a composition is exemplified in DE-PS 22 09 526 in which the dye yellow-orange S 15985 was selected for incorporation into the capsule shell together with an opacifier. As a rule such capsule shells are sensitive to temperature-changes and in this particular case also, complete stability against decomposition of the active constituent cannot be guaranteed.

Liquid formulations containing dihydropyridines are exemplfied in DE-OS 33 07 422. Such liquid pharmaceutical preparations containing nifedipine, although showing a relatively rapid onset of action following sublingual administration, produce only relatively low plasma-concentrations in the phase immediately following administration.

A comparison of the modes of action of nifedipine after oral and sublingual application is to be found in, "Nifedipine serum concentrations following sublingual and oral doses" (Brown et al, International Journal of Clinical Pharmacology, Therapy and Toxicology, Vol. 24, No. 6, 1986, pp 283–286). According to this paper, it was observed that oral administration leads to higher maximum plasma levels and therefore to a very good effect, whereas sublingual administration is characterized by a rapid onset of action with reduced maximum plasma levels. These differences in effect are attributed to the fact that upon sublingual administration, there is an initial precipitation of nifedipine crystals in the saliva such that only a portion of the nifedipine applied is absorbed, whilst the remaining portion, which has precipitated as crystals, dissolves and reaches the circulation at a later time.

An object of the present invention, therefore, is to produce a pharmaceutical composition containing nifedipine which, when compared with known presentations, is distinguished by a more rapid sublingual absorption and a high plasma-concentration in short time after sublingual adminstration. The compositions of the present invention should possess a high degree of stability and are suitable for rapid and unrestricted administration in the absence of medical assistance.

In order to achieve this, the invented pharmaceutical preparation comprises a solution of the active drug together with polyalcohols, such as polyethylene and/or polyalkyleneglycols and/or polyethylene glycol alkyl phenyl ethers and/or polyglycerine fatty acid esters and/or glycerine-polyethyleneglycol oxyfatty acid esters such as glycerine-polyethyleneglycol oxyoleate and/or glycerine-polyethyleneglycoloxystearate and/or partial fatty acid esters of sorbitol or polyhydroxyethylene sorbitol and/or polyvinylalcohols and/or polyhydroxyethylene aliphatic acid esters of polyhydroxy ethylene aliphatic alcohol ethers and/or polyhydroxyethylenepolyhydroxypropylene condensates and/or acrylic acid-methacrylic acid copolymers and/or methacrylic acid ester-acrylic acid ester copolymers and/or methacrylic acid-methacrylic acid methyl ester copolymers and/or acrylic acid ethyl ester-methacrylic acid copolymers and/or polyvinylpyrrolidones and/or alkylene carbonates or copolyvidone in a weight ratio of 1:2 to 1:25 (nifedipine:solvent), the formulation in addition contains ethanol or where required, at least a proportional replacement thereof with medium-chain fatty acid di- and/or -triglycerides in a weight ratio of 1:25 to 1:4 (nifedipine:ethanol) and also a propellant.

The term "polyalcohols" means compounds with at least two unreacted hydroxy groups, especially polymer compounds in which monomer unit at least one unreactable hydroxy group is contained.

The term "medium-chain fatty acid triglycerides" means triglycerides of saturated fatty acids with a chain length between 8 and 12 carbon atoms, especially saturated fatty acids with a chain length from 8 to 10 carbon atoms.

In addition to the solvent and propellant, further pharmaceutical excipients, in particular aromatizers, softeners and inert fillers can be incorporated according to normal pharmaceutical practice. An advantage of using the aerosol method of administration is that the solution of nifedipine can be packaged in a light-excluding aerosol dispensing container thereby preventing photo-decomposition from taking place. By adhering to the nifedpine:solvent weight ratios described above, it has surprisingly been found that a stable solution is formed which facilitates extremely rapid absorption and a significantly greater extent of absorption as compared to other formulations, paraticularly if the polyalcohols, such as polyethylene and polyalkylene glycols and the especially preferred glycerine-polyethyleneglycoloxystearate, polyvinylpyrrolidone, copolyvidone, propylene carbonate and acrylic acid ethylester-methacrylic acid copolymers are used. The choice of these solvents in the weight ratios indicated relative to nifedipine, permits stable solutions to be maintained, even using large quantities of propellant. It has been shown, surprisingly, that in the case of glycerine-polyethyleneglycoloxystearate, in which nifedipine is comparatively more soluble, higher proportions of glycerine-polyethyleneglycoloxystearate are preferable since, in the context of the range given, these higher proportions produce more rapid absorption as a result of greater solubility. Bearing in the mind the fact that the pharmaceutical composition is formulation for aerosol administration, ethanol, in the amounts stated, is of benefit as the miscibility of the solvent with the propellants is thereby improved. It has been demonstrated that adhering to the weight ratios of 1:25 to 1:4, nifedipine:alcohol, in the presence of 40% propellant, results in a clear solution of nifedipine in the solvents listed above, particularly in the case of the first three solvents mentioned, whereby the proportion of alcohol can be reduced as the amount of solvent increases. Replacement of the alcohol by medium-chain fatty acid triglycerides is particularly beneficial when using propylene carbonate additives.

Preferably the maximum water content is 7,5% (by weight) relative to the total weight of the solution thereby reducing still further the tendency of the components of the compositions to separate.

The preferred means of achieving solutions of nifedipine in admixture with water which are stable over a long period after administration and which mix with water after administration, is by adding polyvinypyrolidone (PVP) and/or copolyvidone and/or acrylic acid ethyl ester-methacrylic acid copolymer as solubilising agents. It has, surprisingly, been shown that addition of polyvinylpyrrolidone and/or copolyvidone (a copolymer of polyvinylpyrrolidone and polyvinylacetate) and/or acrylic acid ethyl ester-methacrylic acid copolymers in amounts of 25 to 300 weight%, particularly 50 to 200 weight% relative to the nifedipine content, variably influences the solubility of nifedipine in water, such that a rapid onset of action, characteristic of suglingual administraion, and simultaneously high plasma concentrations can be achieved by adjusting the quantity of polyvinylpyrrolidone and/or copolyvidone and/or acrylic acid ethyl ester-methacrylic acid copolymer in the liquid formulation. In this context the preferred content of PVP and/or copolyvidone and/or acrylic acid ethyl ester-methacrylic acid copolymers approximately amounts to 1-2 fold that of the active constituent. Other expients, such as urea, hydroxymethyl cellulose and other polymers which are presently regarded as pharmacologically acceptable, have not brought to light this surprising effect.

The particularly rapid onset of action and simultaneous high plasma concentration compared with conventional capsule formulations containing polyvinylpyrrolidone, is attributed to the fact that in the liquid compositions disclosed in the invention, polyvinylpyrrolidone is used only in conjunction with ethanol.

High plasma concentrations and rapid onset of action are also achieved by the use of propylene carbonate as a solubilising agent. Such compositions containing propylene carbonate preferably contain $25 \geqq 40$ weight%, especially 30-35 weight% of propellant. For these formulations it was surprisingly observed that the use of propellant volumes which are too high resulted in an almost instantaneous precipitation of nifedipine after spraying onto water or saliva and that by the use of propellant volumes which are too low resulted a non sprayable solution. If however, amounts of propellant, ranging between 25-40 weight%, especially 30-35 weight%, are used in the composition observing a ratio nifedipine to propylene carbonate from 1:6 to 1:10 and nifedipine to fatty acid triglycerides from 1:6 to 1:10, oily formulations, in which the nifedipine remains dissolved in oil, which are stable for periods of 20 minutes after spraying onto water, can be produced.

If in addition to the presence of the solubiliser propylene carbonate, a further solubilising agent such as copolyvidone is present in the mixture, there is a separation of the oily substance into aqueous and oily phases in which the nifedipine crystallises out of the aqueous phase. In order to avoid such unwanted disadvantages, it is preferred that when using propylene carbonate in the formulation, there is no addition of copolyvidone, because in compositions which in addition to propylene carbonate do not contain copolyvidone, the nifedipine remains in the oil phase and is absorbed from this oil phase after sublingual application.

Thus, in a preferred aspect of the invention, there is provided a composition as defined hereinabove, having improved oral absorption after sublingual administration, which contains PVP, copolyvidone, acrylic acid ethyl estermethacrylic acid copolymers or propylene carbonate, particularly in combination with the solvent glycerine-polyethyleneglycoloxystearate, whereby especially in a combination of copolyvidone and glycerine-polyethyleneglycoloxystearate a precipitation of nifedipine after the application or the mixing with water can be avoided for a longer time, such as 15 to 20 minutes.

The precipitation observed following sublingual application of known capsular copositions consisting of 1 part by weight nifedipine, of 15 to 35 parts by weight polyethylene glycol (average molecular weight 300 to 600), of 1 to 10 parts by weight glycerine leads to a form of retarding effect, which results in a slower rise in the plasma concentration and lower maximal plasma concentrations. As a result (non-sublingual) oral administration of conventional presentations affords a higher, usually two-fold, maximum plasma concentration after a given time. The time to peak plasma concentration following sublingual administration of conventional dose forms is typically twice that observed after oral administration.

According to the present invention, it has surprisingly been shown that, after sublingual administration, the plasma concentration is inversely proportional to the amount of PVP and/or copolyvidone, and can be adjusted accordingly. Thus, in accordance with the invention, the composition is adjusted in such a way that the amount of PVP and/or copolyvidone is greater so as to afford more rapid absorption and high peak plasma nifedipine concentrations.

The copolyvidone used in compositions of the present invention advantageously can be a copolymer of 60% PVP and 40% polyvinyl acetate (PVA).

Compositions which possess a particularly rapid onset of effect, produce a high plasma concentration and are also stable in the long term are formulated such that 150 mg contains: 5 mg nifedipine, 40-55 mg glycerine-polyethyleneglycoloxystearate, 20-35 mg ethanol, 5-15 mg copolyvidone or polyvinylpyrrolidone or acrylic acid ethyl ester-methacrylic acid copolymers or mixtures thereof and 55-70 mg of propellant.

The present invention also provides a process for the preparation of the copositions described hereinabove, which process comprises the dissolution of the nifedipine and a solubilising agent and/or solvent selected from the group polyalcohols such as polyethylene glycol and/or polyalkylene glycol and/or alkylphenyl ethers of polyethylene glycol and/or polyglycerine fatty acid esters and/or glycerine-polyethyleneglycoloxy fatty acid esters such as glycerine-polyethyleneglycol oxystearate and/or partial fatty acid esters of sorbitol or polyhydroxyethylene sorbitol and/or polyvinyl alcohols and/or polyhydroxyethylene fatty alcohol ethers or polyhydroxyethylene fatty acid esters and/or polyhydroxypropylenepolyhydroxyethylene condensates and/or methacrylic acid-acrylic acid copolymers and/or methacrylic acid ester-acrylic acid ester copolymers and/or methacrylic acid-methacrylic acid methylester copolymers and/or acrylic acid ethyl ester-methacrylic acid copolymers and/or polyvinylpyrrolidone and/or copolyvidone and/or alkylene carbonates are present in the weight ratio between 1:2 and 1:25 (nifedipine:solvent) and filling the solution together with ethanol in the weight ratio between 1:25 and 1:4 (nifedipine:ethanol) into light-excluding aerosol cans together with an inert and well tolerated pharmaceutical propellant and excipients as appropriate. In the context of the process, the useof glycerine-polyethyleneglycoloxystearate is especially preferred, whereby correspondingly higher amounts of glycerine-polyethyleneglycoloxystearate are again advantageous for aerosol actuations of over 100 mg and particularly those over 150 mg.

The compositions of the present invention are particularly suitable in circumstances where actuations of between 2 and 20 mg, preferbly between 5 and 10 mg, of nifedipine, are delivered and where each actuation delivers a total of 100–500 mg, preferably 150–320 mg, of the composition. The use of polyalcohols and glycerine-polyethyleneglycoloxystearate as well as lecithin and the other named solvents and solubilising agents, permits droplet sizes of greater than 10 microns diameter to be obtained thereby affording rapid absorption of the composition. Flavourings, in particular peppermint oil or similar substances, can be incorporated in addition to other pharmaceutical excipients.

The lower limit stipulated in the invention of 1:2, preferably 1:5 for the weight ratio of nifedipine:polyalcohol, ensures that a stable solution is achieved, which does not tend towards precipitation. The upper limit for the ratio of 1:25 nifedipine:polyalcohol, was chosen in view of rapid absorption and faster onset of effect with sublingual administration and so that no sepearation occurs when combined with ethanol and propellant.

The significant advantages of the invention compared with known compositions are illustrated by the comparative studies shown in the Figs. Diagramms 1–3 depict comparative absorptionkinetics for nifedipine during the first 15 minutes as based upon measurements of serum nifedipine concentrations. FIG. 4 depicts the mean values for the 3 volunteers shown in FIGS. 1–3. FIGS. 5–7 show the relative bioavailabilities over eight hours for a second composition containing nifedipine-serum nifedipine concentrations being measured. FIG. 8 shows a separate curve for the mean values obtained from the volunteers. The values on the ordinate are in nanograms per liter, those on the abscissa represent time. FIGS. 9–13 show the extinctions from sprays containing nifedipine following administration in water, each incorporating differing amounts of polyvinylpyrrolidone or copolyvidone. The standard used in FIGS. 1–4 comprised 150 mg in total, containing 5 mg nifedipine, 40 mg glycerine-polyethyleneglycoloxystearate, 50 mg ethanol, 0,1 mg peppermint oil, 0,3 mg glycerine, 0.05 mg saccharine sodium, 0,25 mg water and 54,3 mg propellant (halogenated fluorohydrocarbons). This substance was compared with commercially available nifedipine chewable capsules. The values which can be achieved from one actuation of the composition of the present invention are reproduced in line 1; those for the comparison afteer sublingual application of the chewable capsules in line 2. These indicate that all 3 volunteers had detectable nifedipine serum levels from the invention after 2 minutes, whilst in comparison none had detectable levels within this time span from the chewable capsule. Following a brief decline in concentration, occurring after a delay with the chewable capsule, there is a constant increase which, compared with the chewable capsule, achieves a notably higher and earlier maximum. Minimum active drug concentrations are therefore achieved much sooner with the spray presentation of the present invention than with conventional formulations.

The standard used in FIGS. 5–8 consisted of a spray containing 150 mg in total, with 5 mg nifedipine, 50 mg glycerine-polyethyleneglycoloxystearate, 30 mg ethanol, 5 mg copolyvidone and 60 mg propellant (halogenated fluorohydrocarbons). In this study also, the spray sample was compared with commercially available nifedipine chewable capsules. The spray was administered sublingually whilst the capsules were swalloed whole with water. The values obtained from one actuation of the spray composition are depicted by line 1 those for the comparison by line 2. The studies show that in the first volunteer, nifedipine could be demonstrated in the serum after 8 minutes and that after 15 minutes all volunteers had levels above 12 ng/ml. At this point in time, following administration of capsules, only one individual had a serum nifedipine-level of 1,7 ng/ml. After 30–45 minutes the maximum serum concentration was reached, both after use of the spray and the chewable capsule. After reaching the peak serum concentrtion, the drug level achieved by the spray remained above that for the capsule over 8 hours. Thus, administration of the spray formulation affords effective nifedipine concentrations significantly earlier than is the case with the capsules and, moreover, the drug levels are sustained for a greater period of time. The area under the curve, which is a measure of the amount of drug in the body, is approximately 40% greater with the spray than with the capsule.

Surprisingly, it has also been possible, according to the present invention, to adjust the compositions such that the mean maximal plasma concentrations following sublingual administration are comparable to those obtained from conventional compositions intended for oral use. This means a more rapid onset of action, an equivalent therapeutic effect and a longer duration of therapeutic effect.

Further advantages arising from the compositions of the present invention are illustrated in the examples set forth below.

The examples depicted in FIGS. 9–13 clearly show the controllability of the water-solubility of nifedipine in liquid presentations such as, for example, a spray. By the addition of PVP or PVP-copolymers to spray solutions of nifedipine, it is not, however likely to be possible to totally avoid precipitation of nifedipine crystals in the mouth after administration with only a small quantity of a solvent, although these crystals will dissolve fairly quickly upon being diluted in water or in the fluid content of the stomach, after which the drug will be available for absorption. In this way and to achieve the desired characteristics it is possible to adjust for differences in blood levels resulting after sublingual and oral administration.

Water solubility was determined by measurement of the extinction at 350 nm against time. To simulate the conditions of sublingual administration equivalent volumes of product and saliva were mixed and allowed to stand for 10 minutes after which, volume was made up to 900 ml with water and measurement took place in accordance with the dissolution test method described in the USP. Temperature was maintained at a constant 37° C.+0,5° C. and the anticipated crystals were allowed to form during the first 10 minutes.

In the comparative analysis of sprays containing PEG it was found that two actuations of a 5 mg nifedipine spray show an extinction at 350 nm of 0,014 after 5 minutes and 0,031 after 20 minutes. The profile of the curve was flat and the addition of 10 mg copolyvidone produced a distinct increase in gradient with extinction after 5 minutes=0,021, and 0,057 after 20 minutes. The actuations were diluted 1:1 with water in order to simulate conditions during sublingual administration.

Figure 9:
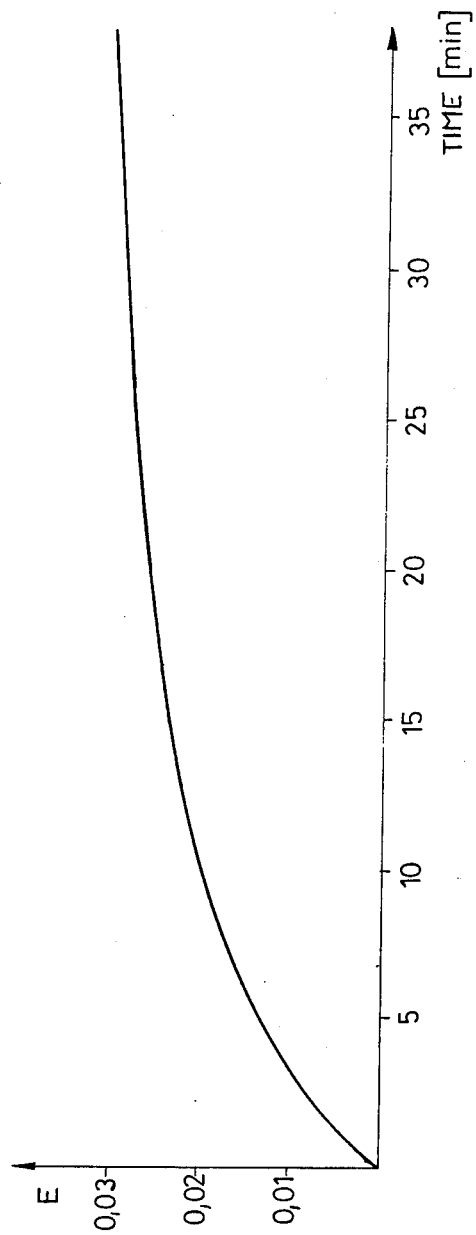
Figure 10:
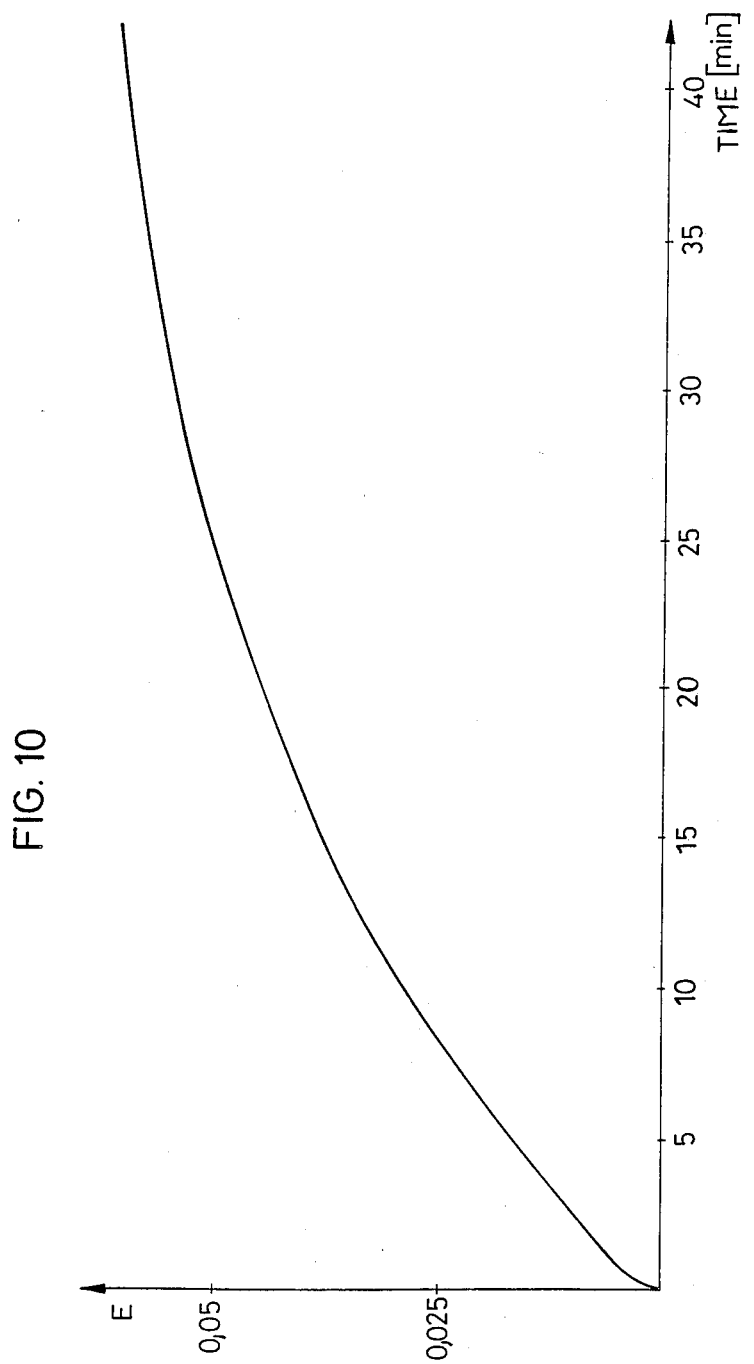
Figure 11:
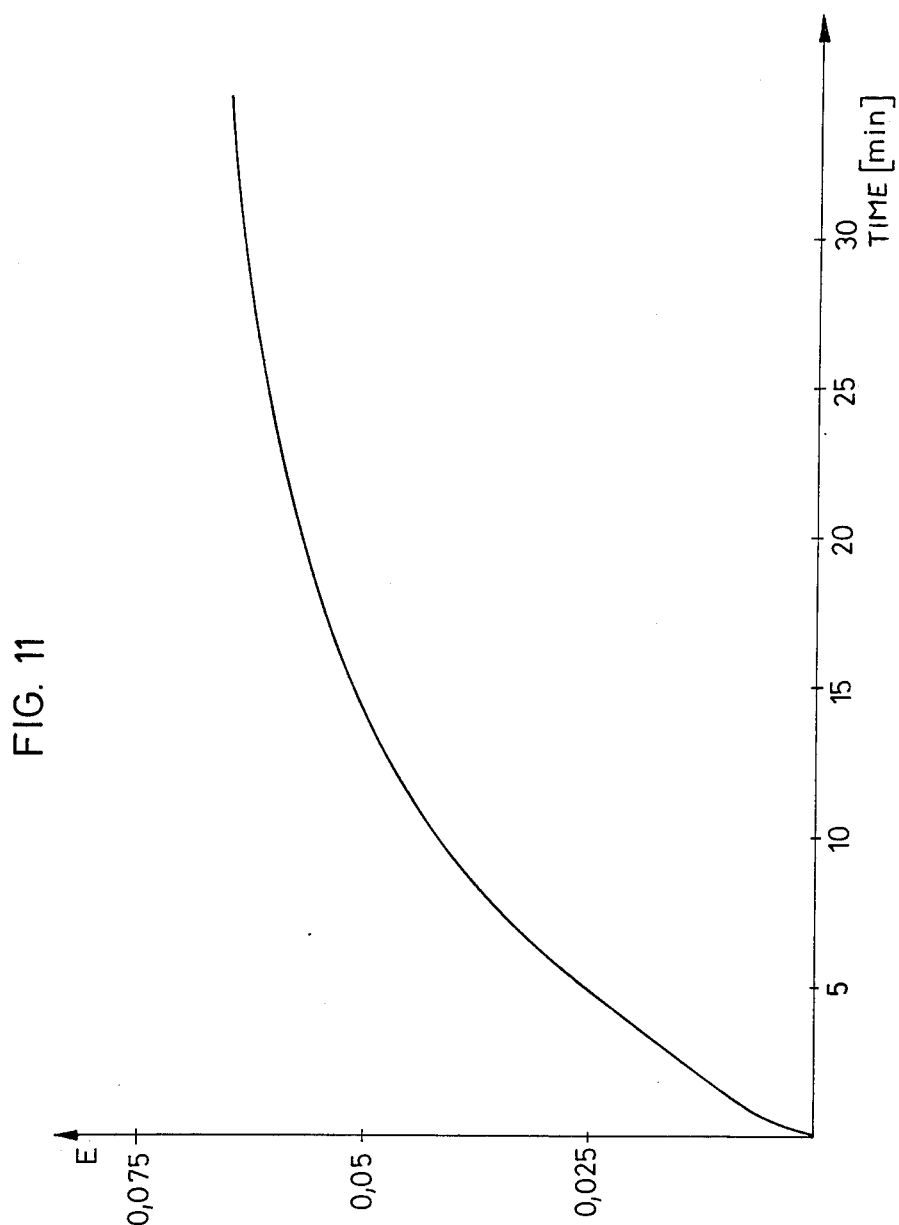

In comparisons using continuously increasing addition of copolyvidone, it was observed that a spray containing the same amount of active constituent without the addition of copolyvidone produced an extinction of 0,013 and 0,026 after 5 and 20 minutes respectively. After addition of copolyvidone (5 mg) values of 0,020 and 0,045 were obtained after 5 and 20 minutes respectively and the curve had already become distinctly steeper in its profile. Upon addition of 10 mg copolyvidone, extinctions were measured at 0,020 and 0,052 after 5 and 20 minuted respectively whereas addition of 15 mg copolyvidone causes the values to rise markedly with extinction after 5 minutes amounting to 0,024 and that after 20 minutes to 0,033. Finally the addition of 20 mg copolyvidone produced extinctions after 5 and 20 minutes of 0,033 and 0,078 respectively. The relationships for a spray containing no copolyvidone are depicted in FIG. 9. The distinct change in the curve after addition of 5 mg copolyvidone to a spary corresponding to that in FIG. 9 is shown in FIG. 10. Finally, FIG. 11 shows the typically steeper profile after addition of 15 mg copolyvidone.

Figure 12:
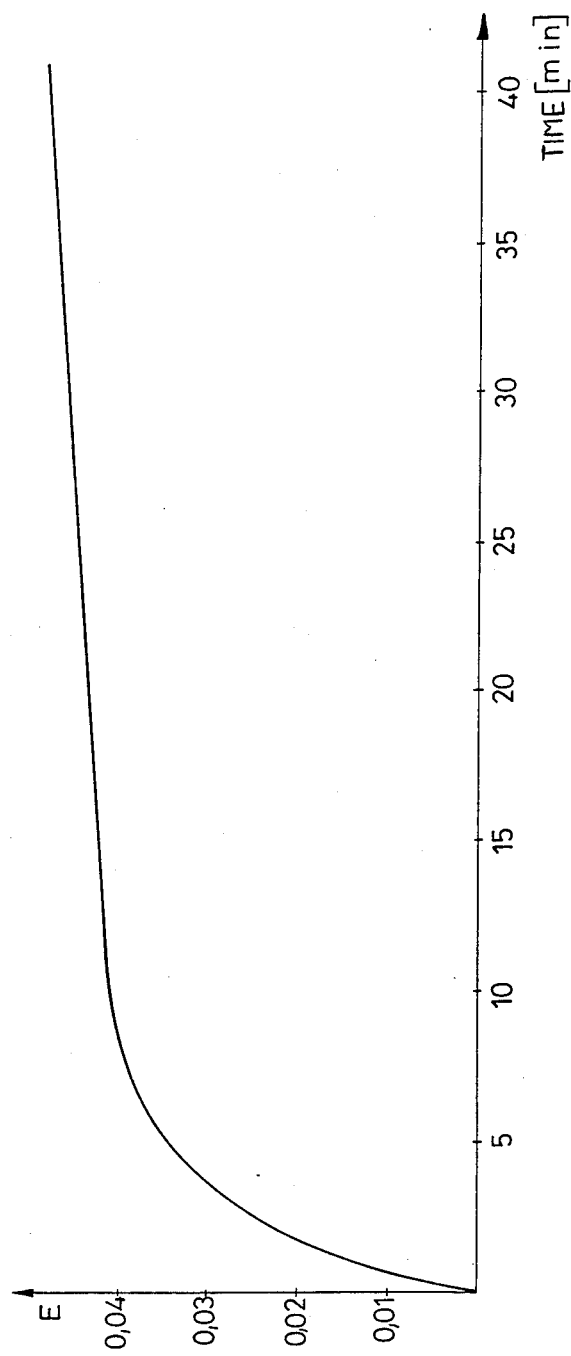
Figure 13:
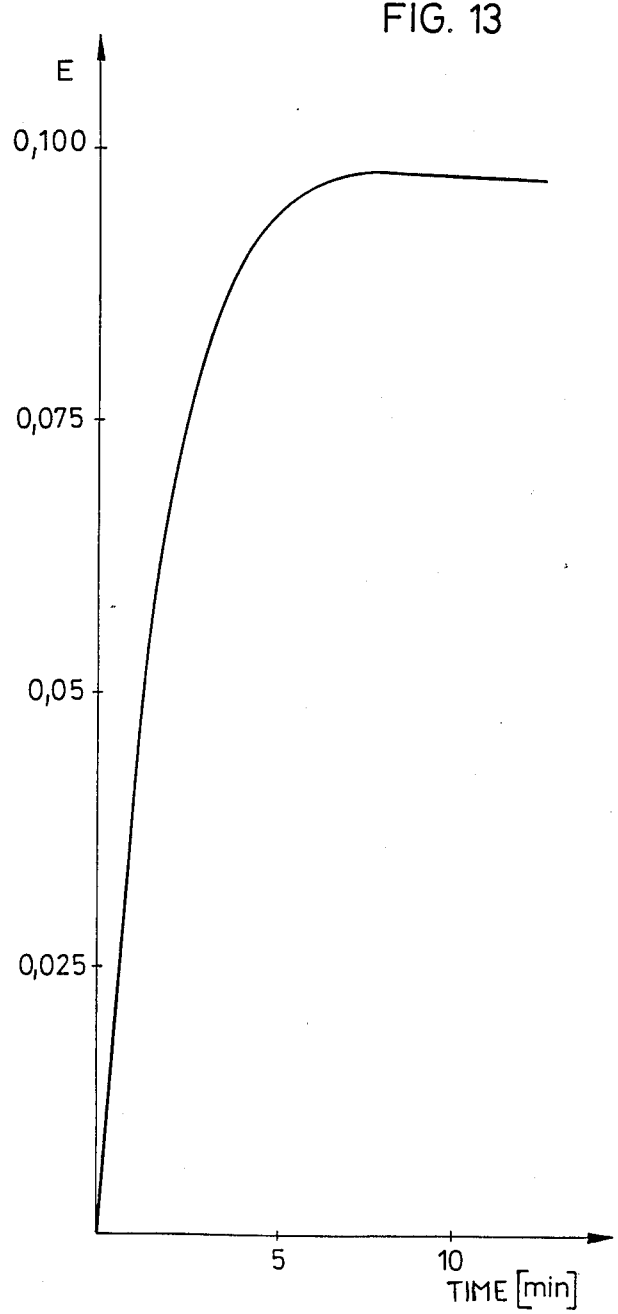

On dilution of such a spray with water in a volume relationship of 1:5 relative to the volume of the maximal spray actuation, the extinction in the absence of copolyvidone measures 0,034 after 5 minutes and 0,045 after 20 minutes, i.e., a flat profile as depicted in FIG. 12. After addition of 10 mg copolyvidone the curve shown in FIG. 13 was obtained, with an extinction after 5 minutes of 0,095. After six minutes the maximum value of 0,098 was recorded. A correspondingly improved formulation containing glycerine-polyethyleneglycoloxystearate also showed a clear concentration dependant improvement relative to the amount of copolyvidone added. In the absence of copolyvidone, extinction values of 0,028 and 0,049 were obtained after 5 and 20 minutes thus exhibiting an average profile. The addition of 10 mg copolyvidone increased the values for the 5 and 20 minutes extinction values to 0,036 and 0,056 respectively. 5 mg copolyvidone produced a maximum extinction value of 0,072 after 2 minutes so producing a much steeper profile curve. Analogous results are obtained with formulations in which copolyvidone is replaced by corresponding amounts of polyvinylpyrrolidone or acrylic acid ethyl ester-methacrylic acid copolymers or mixtures thereof.

EXAMPLE 1

Four formulations containing nifedipine were studied under conditions simulating sublingual administration in order to determine their stabilitiy under such conditions.

| mg content | I | II | III | IV |
|---|---|---|---|---|
| Nifedipine | 5 | 5 | 5 | 5 |
| Glycerin-polyethylene-glycoloxystearate | 50 | 50 | 50 | 50 |
| Ethanol | 30 | 30 | 25 | 30 |
| Propellant | 65 | 60 | 60 | 60 |
| Copolyvidone | — | 5 | 10 | 10 |
| | 150 | 150 | 150 | 150 |

0.1 ml of water is placed in a watch glass and an actuation of 160 mg is added and left for 30 seconds after which a further 0.2 ml of water is added.

In the case of formulation I, clouding of the solution, attributable to nifedipine precipitation, is observed 4 minutes after the addition of water.

In the case of formulation II, small nifedipine crystals can be observed on the watch glass after 30 minutes. Only after 50 minutes does nifedipine precipitate from formulations III and IV, whereby formulation III is slightly more stable than formulation IV since the amount of precipitating nifedipine is significantly less.

These results show that formulations II–IV are suitable for sublingual application, and that formulation III because of its exceptionally good stability is the best suited. This is attributable to the presence of relatively high levels of copolyvidone and glycerine-polyethyleneglycoloxystearate. Analogous results are achieved with formulations in which copolyvidone is replaced with corresponding amounts of polyvinylpyrrolidone or acrylic acid ethyl ester-methacrylic acid copolymers or mixtures thereof.

EXAMPLE 2

Four formulations containing nifedipine and propylene carbonate as solubilising agent were studied under conditions simulating sublingual administration in order to determine their stability under such conditions.

| mg content | I | II | III | IV |
|---|---|---|---|---|
| Nifedipine | 5 | 5 | 5 | 5 |
| Ethanol | 20 | 10 | 10 | — |
| Propylene carbonate | 40 | 50 | 30 | 50 |
| Polyethylene glycol | 20 | — | — | — |
| Medium-chain fatty acid triglyceride | — | 40 | 35 | 50 |
| Glycerin-polyethylene-glycoloxystearate | — | — | 10 | — |
| Propellant | 65 | 50 | 60 | 50 |
| | 150 | 155 | 150 | 155 |

For each of these formulations, an actuation of 150 mg was placed on a watch-glass containing 0.3 ml water. In a second test an actuation of the formulation was placed upon a dry watch-glass and 0.3 ml of water was subsequently added. It was then observed whether or not nifedipine precipitated from the clear oily formulation.

In both cases with formulation I. nifedipine precipitated immediately whilst, in contrast, formulation II in both cases remained as a clear oily liquid over a period of 20 minutes.

In the first test on formulation III (water already present), nifedipine precipitated immediately, whilst in the second test the soluton remained clear.

Formulation IV, similarly to II in both tests remains a clear, oily liquid for at least 20 minutes.

It is apparent from these results that formulation II, i.e. that with the highest proportion of propylene carbonate and lowest propellant constant, is particularly suited for the purpose of sublingual administration.

EXAMPLE 3

Three formulations containing nifedipine were studied under conditions simulating sublingual administration in order to determine their stability under such conditions.

| mg content | I | II | III |
|---|---|---|---|
| Nifedipine | 5 | 5 | 5 |
| Acrylic acid ethyl ester-methacrylic acid copolymer | — | 5 | 5 |
| Glycerine-polyethylene-glycoloxysearate | 50 | 50 | 50 |
| Ethanol | 30 | 40 | 50 |
| Propellant | 65 | 60 | 60 |
|  | 150 | 160 | 160 |

For each of these formulations an actuation of 150 mg was placed on a watch-glass containing 0.3 ml water. In a second test an actuation of the formulation was placed upon a dry watch-glass and 0.3 ml of water was subsequently added. It was then observed whether or not nifedipine precipitated from the clear oily formulation.

In the case of formulation I clouding of the solution, attributable to nifedipine precipitation, is observed 4 minutes after the spraying.

In the first test on formulation II and III (water already present) nifedipine precipitated immediately, which however dissolves by further addition of water.

In the second test no precipitation of nifedipine is observed after the spraying. Only after addition of water nifedipine precipitates, whereafter the crystals dissolve by further dilution with water.

It is apparent from these results that formulation II and III are particularly suited for the purpose of sublingual administration, as through the permanent dilution with water by the saliva occurs a rapid dissolution of the precipitated nifedipine crystals.

A further example of the invented formulation consists of mixing 5 mg nifedipine, 70 mg glycerine-polyethyleneglycoloxystyrate and 30 mg ethanol together with 55 mg of a propellant (halogenated fluorohydrocarbon) in order to form a dosable aerosol spray.

For the purpose of producing a 10 mg spray, a correspondingly large valve was used and the following advantegous composition was chosen, each 150 mg containing: 5.5 mg nifedipine, 40 mg glycerine polyethyleneglycoloxystearate, 49.5 mg ethanol, peppermint oil, glycerine, saccharin sodium in the usual amounts, plus 0.25 mg water and 54.3 mg of propellant (halogenated fluorohydrocarbon). This formulation was delivered in an actuation amounting to 270 mg, thus providing a dose of 10 mg nifedipine per actuation.

In all cases, compositions could be achieved which are particularly stable even at low temperatures and which, in addition to having distinctively improved stability had an especially rapid onset of action.

We claim:

1. A pharmaceutical composition suitable for the treatment of coronary heart disease, comprising nifedipine as the active ingredient, said nifedipine being present as a solution, wherein said solution in addition to the active ingredient comprises:

(a) at least a first solvent which is ethanol, which is optionally at least partially replaced by a medium-chain fatty acid triglyceride in a weight ratio of 1:25 to 1:4 (nifedpine:first solvent);

(b) at least a co-solvent selected from the group consisting of polyalcohols, alkylphenylethers of polyethylene glycol, polygylcerine fatty acid esters, glycerine-polyethylene glycoloxy fatty acid esters, partial fatty acid esters of sorbitol, partial fatty acid esters of polyhydroxy ethylene sorbitol, polyvinyl alcohols, polyhydroxy ethylene aliphatic acid esters and polyhydroxy ethylene-polyhydroxypropylene condensates;

(c) a solubilizing agent selected from the group consisting of acrylic acid-methacrylic acid copolymers, methacrylic acid ester-acrylic acid ester copolymers, methacrylic acid-methacrylic acid methyl ester copolymers, methacrylic acid-acrylic acid ethyl ester copolymers, polyvinylpyrrolidones, alkylenecarbonates and copolyvidone in a weight ratio of 1:2 to 1:25 (nifedipine:co-solvent and solubilizing agent); and (d) a propellant.

2. A composition according to claim 1, wherein said polyalcohols are selected form the group consisting of polyethylenglycols and polyalkyleneglycols.

3. A composition according to claim 1, wherein said glycerine polyethyleneglycoloxy fatty acid esters are selected from the group consisting of glycerine-polyethylene glycoloxyoleate and glycerine-polyethyleneglycol stearate.

4. A liquid pharmaceutical composition suitable for aerosol administration in the treatment of coronary heart disease, comprising nifedipine, ethanol as a solvent therefor and a propellant held within an aerosol-dispensing container, said composition further comprising a co-solvent which is a polyalcohol, at least a part of the ethanol being optionally replaced by a medium-chain fatty acid triglyceride, and one or more solubilizing agents selected from the group consisting of polyalcohols, polyvinylpyrrolidone, alkylene carbonates, copolyvidone and acrylic acid ethyl ester-methacrylic acid copolymers, wherein the weight ratio of nifedipine:ethanol medium-chain fatty acid triglyceride is in the range 1:25 to 1:4 and the weight ratio of nifedipine:co-solvent is in the range 1:2 to 1:25, provided that:

(i) when the polyalcohol is polythylene glycol, there is additionally present one or more other polyalcohols and/or a said solubilizing agent and/or at least part of the ethanol is replaced by a medium-chain fatty acid triglyceride; and (ii) when the polyalcohol is glycerine-polyethylene glycoloxystearate, the ratio of propellant:nifedipine is less than 220 and/or at least part of the ethanol is replaced by a medium-chain fatty acid triglyceride.

5. A composition according to claim 1, wherein the formulation contains a maximum of 7.5 weight % of water relative to the total weight of the solution.

6. A composition according to claim 1, wherein the solubilizing agent is selected from the group consisting of copolyvidone, PVP, and acrylic acid ethyl ester-methacrylic acid copolymers and is used in an amount of 25–300 weight %, relative to the nifedipine content.

7. A composition according to claim 6, wherein said solubilizing agent is used in an amount of 50–200 weight % relative to the nifedipine content.

8. A composition according to claim 1, wherein propylene carbonate is used as a solubilizing agent.

9. A composition according to claim 8, wherein, when propylene carbonate is employed, there is no addition of copolyvidone to the formulation.

10. A composition according to claim 8, wherein, when propylene carbonate is used as a solubilizing agent, 25-40% of propellant are present for the purpose of producing a stable, aerosolisable formulation.

11. A composition according to claim 10, wherein 30-35 weight % of propellant are present.

12. A composition according to claim 1, wherein, when propylene carbonate is used as a solubilizing agent, ethanol is at least partly replaced by medium-chain fatty chain triglycerides.

13. A composition according to claim 8, wherein the ratio of nifedipine:propylene carbonate is in the range 1:6 to 1:10 and the ratio of nifedipine:medium-chain fatty acid triglycerides is in the range 1:6 to 1:10.

14. A composition according to claim 1, wherein a copolymer of 60% polyvinylpyrrolidone and 40% polyvinyl acetate is used.

15. A composition according to claim 1, wherein 150 mg of the composition contains 5 mg nifedipine, 40-55 mg glycerine-polyethylene glycoloxystearate, 20-35 mg ethanol, 5-15 mg of a further co-solvent selected from the group consisting of copolyvidone, polyvinylpyrrolidone, polyacrylic acid and mixtures thereof, and 55-70 mg propellant.

16. A composition according to claim 1, wherein said solution, in addition to nifedipine, comprises ethanol, glycerine-polyethyleneglycoloxystearate, copolyvidone and a propellant.

17. Process for the manufacture of a dosable sublingually administerable pharmaceutical preparation with nifedipine as the active ingredient, comprising:

dissolving the active ingredient in a solution comprising:
(a) at least a first solvent which is ethanol, which is optionally at least partially replaced by a medium-chain fatty acid triglyceride in a weight ratio of 1:25 to 1:4 (nifedipine:first solvent);
(b) at least a co-solvent selected from the group consisting of polyalcohols, alkylphenylethers of poly ethyleneglycol, polyglycerine fatty acid esters, glycerine-polyethyleneglycoloxy fatty acid esters, partial fatty acid esters of sorbitol, partial fatty acid esters of polyhydroxyethylene sorbitol, polyvinylalcohols, polyhydroxy ethylene aliphatic acid esters and polyhydroxyethylene-polyhydroxypropylene condensates;
(c) a solubilizing agent selected from the group consisting of acrylic acid-methacrylic acid copolymers, methacrylic acid ester-acrylic acid ester copolymers, methacrylic acid-methacrylic acid methyl ester copolymers, methacrylic acid-acrylic acid ethyl ester copolymers, polyvinylpyrrolidones, alkylenecarbonates and copolyvidone in a weight ratio of 1:2 to 1:25 (nifedipine:-co-solvent and solubilizing agent); and
(d) a propellant, and introducing the resulting nifedipine-containing solution, together with an inert and pharmaceutically acceptable propellant and an excipient, into a light-protected aerosol can.

* * * * *